United States Patent [19]

Nakano et al.

[11] Patent Number: 5,079,376
[45] Date of Patent: Jan. 7, 1992

[54] NOVEL SUBSTANCE UCT-1003 AND PROCESS FOR PRODUCING THE SAME

[75] Inventors: Hirofumi Nakano; Yoshinori Yamashita; Katsuhiko Ando; Yutaka Saito, all of Machida; Keiichi Takahashi, Susono; Hiroe Ohno, Numazu, all of Japan

[73] Assignee: Kyowa Hakko Kogyo, Ltd., Tokyo, Japan

[21] Appl. No.: 468,915

[22] Filed: Jan. 23, 1990

[30] Foreign Application Priority Data

Jan. 27, 1989 [JP] Japan .................................. 1-18300

[51] Int. Cl.$^5$ .............................................. C07C 50/22
[52] U.S. Cl. .................................. 552/202; 514/680; 435/127; 435/252.1
[58] Field of Search .......................... 552/202; 514/680

[56] References Cited

U.S. PATENT DOCUMENTS 5,001,243 3/1991 Fischer et al. ...................... 552/202

OTHER PUBLICATIONS

Chemische Berichte, vol. 96, No. 9, pp. 2399-2409; H. Brockmann et al.
Chemische Berichte, vol. 98, No. 10, Oct. 1965, pp. 3145-3152, H. Brockmann et al.

*Primary Examiner*—James H. Reamer
*Attorney, Agent, or Firm*—Antonelli, Terry, Stout & Kraus

[57] ABSTRACT

Disclosed is novel compound UCT-1003 represented by the following formula:

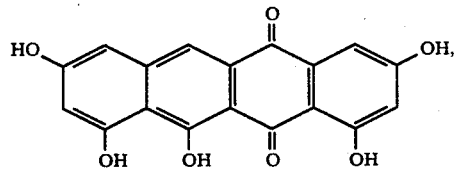

and having anti-tumor activity. UCT-1003 is produced by culturing a microorganism belonging to the genus Paecilomyces.

2 Claims, 1 Drawing Sheet

NOVEL SUBSTANCE UCT-1003 AND PROCESS FOR PRODUCING THE SAME

BACKGROUND OF THE INVENTION

The present invention relates to novel substance UCT-1003 and to a process for producing the same.

UCT-1003 has anti-tumor activity and is useful as an anti-tumor agent

Heretofore, many compounds such as anthracycline compounds, anthraquinone compounds and mitomycin compounds have been reported as anti-tumor antibiotics.

As anti-tumor antibiotics having the structures similar to that of UCT-1003, there have been reported anthracycline compounds produced by actinomycetes, such as ciclacidin, bis-anhydroaklavinone, $\eta$-rhodomycinone, $\eta$-isorhodomycinone and $\eta_1$-pyrromycinone (CRC Handbook of Antibiotic Compounds, CRC press, U.S.A., 1981). Further, tetracenomycin D having the structure similar to that of UCT-1003 has been reported (Journal of Bacteriology, August, 1986, p.575–580, p.581–586) However, a compound having the same structure as UCT-1003 is not found in any of these reports, and hence UCT-1003 is a novel substance.

SUMMARY OF THE INVENTION

The present invention provides novel substance UCT-1003 having anti-tumor activity and which is represented by the following formula:

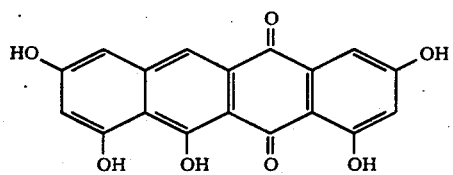

UCT-1003 can be produced by culturing a UCT-1003-producing microorganism belonging to the genus Paecilomyces in a culture medium.

DETAILED DESCRIPTION OF THE INVENTION

Figure 1:
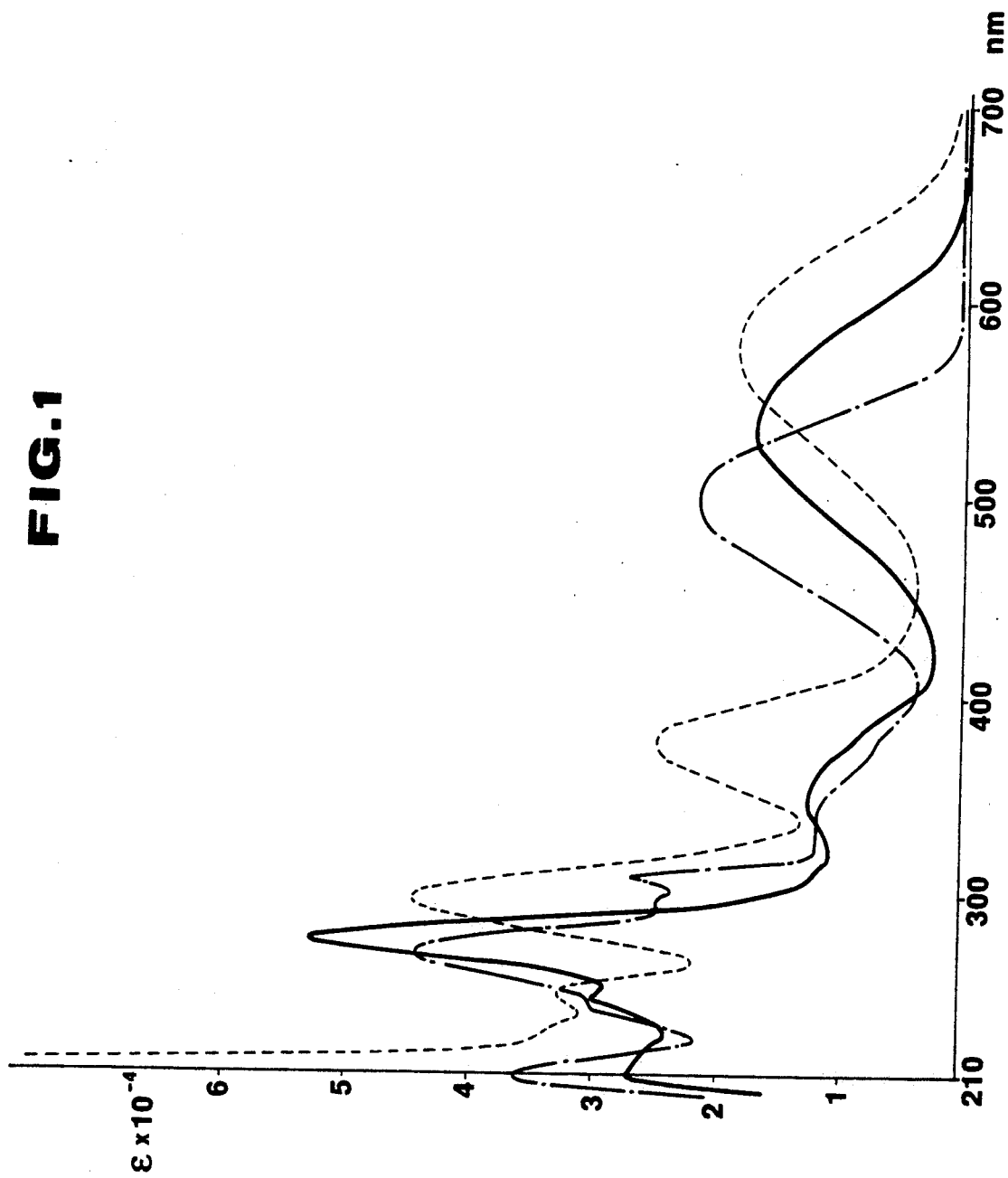
FIG. 1 shows the UV absorption spectra of UCT-1003, in which the solid line, the dotted line and the broken line show the spectra in a neutral solution, a basic solution and an acidic solution, respectively.

Properties of many microorganisms obtained from nature have been studied. As a result, it has been found that a substance having anti-tumor activity is produced in the culture of a microorganism isolated from a soil sample obtained in Yamanashi Prefecture (hereinafter referred to as SPC-13780 strain).

After isolation and purification, the physicochemical properties of the substance have been investigated, whereby it has been found to be a novel compound. The compound has been named UCT-1003.

The physicochemical properties of UCT-1003 are shown below.

(1) Molecular formula: $C_{18}H_{10}O_7$
(2) Molecular weight: 338
(3) HR-EIMS: Found 338.0422; Calcd. 338.0425

(4) Melting point:
Gradually blackens upon heating, showing no clear melting point up to 300° C.

(5) UV absorption spectrum: As shown in FIG. 1
(6) IR absorption spectrum (measured by the KBr method): 3400, 3250, 2930, 1615, 1600, 1580, 1400, 1370, 1330, 1275, 1160 cm$^{-1}$
(7) $^1$H-NMR (400 MHz, DMSO-d$_6$): Major peaks ($\delta$): 6.41 (1H, brs), 6.49 (1H, d, J=2.5), 6.71 (1H, brs), 7.03 (1H, d, J=2.5), 7.63 (1H, s), 10.43 (1H, br), 11.01 (1H, br), 12.68 (1H, br)
(8) 13C-NMR (100 MHz, DMSO-d$_6$): Major peaks ($\delta$): 104.3 (d), 105.5 (s), 105.7 (d), 107.5 (d), 108.0 (d), 110.0 (s), 110.5 (s), 120.0 (d), 128.8 (s), 135.6 (s), 138.9 (s), 160.9 (s), 161.7 (s), 164.2 (s), 164.3 (s), 168.0 (s), 181.3 (s), 186.3 (s)
(9) Solubility in solvents: Readily soluble in dimethylsulfoxide, pyridine, methanol, ethanol and acetone; soluble in chloroform and ethyl acetate; and sparingly soluble in water and n-hexane.
(10) Color and form of the substance; Deep reddish purple powder The biological activities of UCT-1003 are described below.

(A) Antibacterial activity

The minimum inhibitory concentration (MIC) of UCT-1003 against the growth of various bacteria is shown in Table 1. The antibacterial activity was determined by the agar dilution method using a medium (pH 7) which comprises 3 g/l Bacto-Tryptone (Difco Laboratories), 3 g/l meat extract, 1 g/l yeast extract, 1 g/l glucose and 16 g/l agar.

TABLE 1

| Bacteria tested | MIC ($\mu$g/ml) |
| --- | --- |
| Staphylococcus aureus ATCC 6538P | 2.6 |
| Enterococcus faecium ATCC 10541 | 2.6 |
| Bacillus subtilis No. 10707 | 83 |
| Klebsiella pneumoniae ATCC 10031 | >100 |
| Escherichia coli ATCC 26 | >100 |
| Shigella sonnei ATCC 9290 | >100 |
| Salmonella typhi ATCC 9992 | >100 |

(B) Anti-tumor activity against T24 cells

T24 cells were suspended in a medium comprising F10 medium (Gibco Co., Ltd.), 0.1 g/ml fetal calf serum, 100 units/ml penicillin and 100 ug/ml streptomycin (hereinafter referred to as medium A) to a concentration of $2 \times 10^4$ cells/ml. The cell suspension thus prepared was put into wells of a 96-well microtiter plate in the amount of 0.1 ml per well. After incubation at 37° C. for 20 hours in a CO$_2$-incubator, 0.05 ml of a test sample appropriately diluted with medium A was added to each well. The cells were further cultured at 37° C. for 72 hours in the CO$_2$-incubator and the culture supernatant was removed. To the residue was added a medium comprising medium A and 0.02% Neutral Red in the amount of 0.1 ml per well, followed by culturing at 37° C. for one hour in the CO$_2$-incubator, whereby the cells were stained. After removal of the culture supernatant, the residue was washed once with physiological saline.

The pigment was extracted with 0.001N hydrochloric acid/30% ethanol and absorbance at 550 nm was measured by using a microplate reader. The concentration of the test compound at which the growth of the cells is inhibited by 50% (IC$_{50}$) was calculated by comparing the absorbance of untreated cells with those of the cells treated with the test compound at known concentrations. The result is shown in Table 2.

(C) Anti-tumor activity against HeLaS3 cells

HeLaS3 cells were suspended in a medium comprising MEM medium (Nissui Pharmaceutical Co., Ltd.) and 2 mM glutamine to a concentration of $3 \times 10^4$ cells/ml. The cell suspension thus prepared was put into wells of a 96-well microtiter plate in the amount of 0.1 ml per well. The system was treated in the same manner as in the case of T24 cells described above to calculate $IC_{50}$.

The result is also shown in Table 2.

TABLE 2

| Test Compound | $IC_{50}$ (μg/ml, 72 hours) | |
|---|---|---|
| | T24 | HeLaS3 |
| UCT-1003 | 0.13 | 0.35 |

(D) Anti-tumor activity against lymphocytic leukemia P388 tumor

Five male CDF$_1$ mice each having a weight of about 22 g were used for each group as test animals, and $1 \times 10^6$ cells of lymphocytic leukemia P388 tumor cells were intraperitoneally implanted into the animals. Phosphate solution saline (PBS) containing UCT-1003 (0.2 ml) was once administered intraperitoneally 24 hours after the implantation of tumor cells. The composition of PBS was 0.8 g/dl NaCl, 0.02 g/dl KCl, 1.15 g/dl Na$_2$HPO$_4$ and 0.02 g/dl KH$_2$PO$_4$ (pH 7.2). For comparison, 0.2 ml of PBS containing mitomycin C was intraperitoneally administered 24 hours after the implantation of tumor cells. Increased life span determined from mean survival days after the implantation is shown in Table 3 as T/C (T: mean survival days of the test groups, C: mean survival days of the control group which received 0.2 ml of PBS intraperitoneally).

TABLE 3

| Test compound | Dose (mg/kg) | Increased life span (T/C) |
|---|---|---|
| UCT-1003 | 50 | 1.30 |
| | 25 | 1.30 |
| | 12.5 | 1.21 |
| Mitomycin C | 4 | 1.57 |

The results of (B), (C) and (D) described above show that UCT-1003 inhibits the growth of tumor cells and thus can be an effective anti-tumor agent.

The process for producing UCT-1003 is described below.

UCT-1003 can be obtained by culturing a microorganism belonging to the genus Paecilomyces and having an ability to produce UCT-1003 in a medium, allowing UCT-1003 to accumulate in the culture, and recovering UCT-1003 therefrom.

Any strain of the genus Paecilomyces which is capable of producing UCT-1003 may be used for the purpose of the present invention. A typical example of a suitable strain is SPC-13780 strain which was isolated by the present inventors.

The mycological properties of SPC-13780 strain are as follows.

(1) Macroscopic observation

When SPC-13780 strain is cultured at 25° C. on a malt extract agar medium, the diameter of a colony reaches 22 to 24 mm on the seventh day from the start of the culturing. The colony shows a greyish rose color or a flesh color.

When the strain is cultured at 25° C. on a potato glucose agar medium, the diameter of a colony reaches 31 to 32 mm on the tenth day from the start of the culturing. The colony shows a light lilac color or a greyish rose color, and soluble yellowish-green pigment dissolving in the culture medium is observed.

The optimal growth temperature for this strain is in the range of 15° to 30° C., most preferably about 25° C., and the pH range that allows its growth is 3 to 10.

(2) Observation under optical microscope

Hyphae are septate and smooth and branch well. Conidiophores arise from the hyphae, and branch in the upper part in a verticillate form or irregularly, forming two to four phialides on the top of each branch. Phialides are colorless, smooth and lageniform, and taper off to a point. They are 6.5 to 12 μm long and 1.5 to 2.5 μm wide, tapering to 0.2 to 0.4 μm. The conidial ontogeny is enteroblastic. Phialoconidia are unicellular and fusiform or limoniform in shape, and show a golden color. They are 3 to 5 μm long and 1.5 to 2.5 μm wide, and have verruculose or spinulose surfaces. The conidia develop in the form of a long chain from the top of the phialide. Only the anamorph as described above is observed for this strain, with no teleomorph being observed at all.

A taxonomical study of this strain based on the above mycological properties according to "The Genera of Fungi Sporulating in Pure Culture, 2nd Ed., Cramer Vaduz J.A. von Arx, 1974" revealed that it belongs to Paecilomyces sp. The strain was named Paecilomyces sp. SPC-13780 and deposited with the Fermentation Research Institute, Agency of Industrial Science and Technology under the Budapest Treaty with accession number FERM BP-2256 on Jan. 24, 1989. The depository is located at 1-3, Higashi 1 chome, Tsukuba-shi, Ibaraki-ken 305, Japan.

For the culturing of the strains used in the present invention, conventional methods for culturing molds are generally employed. Culture media of any type may be used insofar as appropriate amounts of carbon sources, nitrogen sources, inorganic substances and other nutrients are contained.

As the carbon sources, glucose, starch, glycerol, mannose, fructose, sucrose, molasses, etc. can be used alone or in combination. In addition, hydrocarbons, alcohols, organic acids, etc. may also be used according to the assimilability of the microorganism employed.

As the nitrogen sources, inorganic or organic nitrogen-containing compounds such as ammonium chloride, ammonium sulfate, ammonium nitrate, sodium nitrate and urea, and natural nitrogenous substances such as peptone, meat extract, yeast extract, dry yeast, corn steep liquor, soybean powder and Casamino acid can be used alone or in combination.

As the inorganic substances, sodium chloride, potassium chloride, ferrous sulfate, zinc sulfate, manganese sulfate, copper sulfate, calcium carbonate, phosphates, and other inorganic salts can be used.

If necessary, organic or inorganic substances that promote the production of UCT-1003 such as biotin and vitamins may also be added in appropriate amounts.

As the method of culturing, either of liquid culture and solid culture may be used, but usually liquid culture, especially submerged stirring culture, is used. Culturing temperature is 20° to 35° C., preferably 23° to 28° C. It is desirable to maintain the pH of the medium at 4 to 10, preferably 5 to 7 by adding aqueous ammonia, aqueous ammonium carbonate, etc. to the medium. Usually, by liquid culture for 1 to 7 days, the desired substance is formed and accumulated in the culture. When the amount of the product in the culture reaches the maximum, the culturing is discontinued and the desired substance is isolated and purified from the culture.

For the isolation and purification of UCT-1003 from the culture, an ordinary method for isolating a microbial metabolite from the culture can be utilized. For example, the culture is separated into culture broth and microbial cells by filtration, centrifugation, etc. The microbial cells are extracted with a solvent in which UCT-1003 is soluble such as chloroform and acetone. The extract is concentrated under reduced pressure to remove the solvent, and the residue is dissolved in water to make an aqueous solution. The cell-free culture broth and the solution obtained by treating the microbial cells are treated with a non-ionic porous resin, for example, HP-20 (Mitsubishi Kasei Corporation). Alternatively, the culture may be extracted with a solvent such as chloroform and acetone, followed by removal of the microbial cells by filtration and treatment of the filtrate with a non-ionic porous resin such as HP-20. The active component adsorbed on the non-ionic porous resin is eluted with methanol, acetone, or the like. The eluate is concentrated and the concentrate is adjusted to pH 2 to 4 by the addition of an acid such as sulfuric acid, whereby a precipitate containing UCT-1003 is formed. UCT-1003 thus obtained as a precipitate is dissolved in a solvent such as ethyl acetate and toluene, and the solution is subjected to chromatography using silica gel, etc. to raise the purity. By subsequent crystallization from chloroform-ethyl acetate and the like, pure UCT-1003 is obtained.

During the culture and purification steps, UCT-1003 can be traced by, for example, thin layer chromatography. The $R_f$ value of UCT-1003 in thin layer chromatography using a silica gel plate (Art 5715, Merck Inc.) and a 50:50:10:1 mixture of n-hexane, ethyl acetate, methanol and acetic acid as a developing solvent is 0.49.

When UCT-1003 is used as an anti-tumor composition, the compound is dissolved in physiological saline or a solution of glucose, lactose or mannitol for injection, and usually intravenously administered as an injection in a dose of 0.1 to 100 mg/kg. Alternatively, the compound may be freeze-dried in accordance with the Japanese Pharmacopoeia or may be prepared into injectable powder by adding sodium chloride thereto. Further, the anti-tumor composition may also contain pharmaceutically acceptable well-known diluents, adjuvants and/or carriers such as salts which satisfy requirements for medical use. In cases where the compound is used as an injection, it is sometimes preferred to use auxiliary agents which enhance the solubility. Doses may be appropriately varied depending upon the age and conditions. Administration schedule can also be varied depending upon the conditions and dose. For example, the compound is administered once a day (by single administration or consecutive administration) or intermittently by one to three times a week or once every three weeks. Further, oral administration and rectal administration are also possible in the same dose and in the same manner. The compound can be administered, with appropriate adjuvants, as tablets, powders, granules, syrup, etc. for oral administration and as suppositories for rectal administration.

Certain embodiments of the invention are illustrated by the following representative examples.

EXAMPLE 1

Paecilomyces sp. SPC-13780 (FERM BP-2256) was used as the seed strain. One loopful of the strain was inoculated into 50 ml of a seed medium having the following composition in a 300-ml Erlenmeyer flask, and cultured with shaking at 25° C. for 48 hours.

Composition of the seed medium:

50 g/l peptone, 10 g/l glucose, 5 g/l dry yeast (Ebios), 200 ml/l V8 vegetable juice (Campbell Japan), 0.5 g/l $Mg_3(PO_4)_2 \cdot 8H_2O$ (pH 6.0)

The resulting seed culture was transferred into 18 l of a fermentation medium having the following composition in a 30-l fermentor in the rate of 5% (volume), and culturing was carried out at 25° C. with stirring and aeration (rotation: 350 r.p.m., aeration: 18 l/min).

Composition of the fermentation medium:

50 g/l sucrose, 15 g/l dry yeast, 0.5 g/l $KH_2PO_4$, 0.5 g/l $MgSO_4 \cdot 7H_2O$, 0.5 g/l $Mg_3(PO_4)_2 \cdot 8H_2O$ (adjusted to pH 7.0 with NaOH)

Culturing was carried out for 90 hours without controlling the pH. After the completion of culturing, 15 l of methanol was added to the culture, followed by stirring for 30 minutes. The microbial cells were removed by filtration to obtain 30 l of a filtrate. The obtained filtrate was passed through a column packed with 2 l of a non-ionic porous resin (Diaion HP-20, Mitsubishi Kasei Corporation) to adsorb the active substance. After impurities were eluted with 5 l of water and 5 l of 50% methanol, the active substance was eluted with 5 l of methanol.

The methanol-eluted fraction was concentrated, and the concentrate was adjusted to pH 3 by the addition of sulfuric acid, whereby a precipitate was formed. The precipitate was dissolved in 700 ml of a 8:2 mixture of ethanol and water, and the solution was passed through a DEAE Sepharose column ($CH_3COO$-type, Pharmacia Fine Chemicals, Inc.) to adsorb the active substance. Gradient elution was carried out by gradually adding a 8:2 mixture of ethanol and water containing 0 to 1M ammonium acetate solution to a 8:2 mixture of ethanol and water.

The active fractions obtained were concentrated to make 20 ml of an ethanol solution, which was then passed through a Sephadex $LH_{20}$ column (Pharmacia Fine Chemicals, Inc.), followed by elution with a 8:2 mixture of ethanol and water containing 2 mM ammonium acetate solution. The active fractions obtained were concentrated, and the concentrate was extracted with ethyl acetate solution. The ethyl acetate layer was concentrated to dryness to give 28 mg of UCT-1003 as red powder.

EXAMPLE 2

The same procedure as in Example 1 was repeated except that a fermentation medium of the following composition was used. As a result, 12 mg of UCT-1003 was obtained.

Composition of the fermentation medium:

50 g/l glycerol, 15 g/l dry yeast, 0.5 g/l $KH_2PO_4$, 0.5 g/l $MgSO_4 \cdot 7H_2O$, 0.5 g/l $Mg_3(PO_4)_2 \cdot 8H_2O$ (adjusted to pH 7.0 with NaOH)

What is claimed is:

1. Novel compound NCT-1003 represented by the following formula:

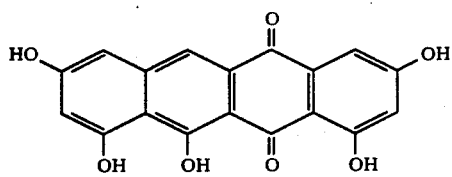
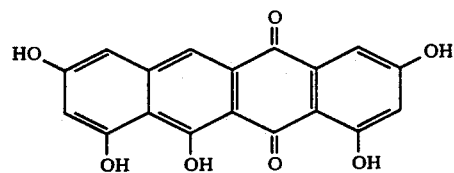
2. A pharmaceutical composition comprising a pharmaceutical carrier and as an active ingredient, an effective amount of UCT-1003.
* * * * *
2. A pharmaceutical composition comprising a pharmaceutical carrier and as an active ingredient, an effective amount of UCT-1003.
* * * * *